United States Patent [19]
Gates et al.

[11] Patent Number: 5,882,630
[45] Date of Patent: Mar. 16, 1999

[54] DENTRIFICE COMPOSITION

[75] Inventors: Cheryl Teresa Gates, Bedfont; Martin Edward Bannon, Cookridge, both of England

[73] Assignee: SmithKline Beecham p.l.c., Brentford, England

[21] Appl. No.: 776,270

[22] PCT Filed: Jul. 18, 1995

[86] PCT No.: PCT/EP95/02826

§ 371 Date: Apr. 3, 1997

§ 102(e) Date: Apr. 3, 1997

[87] PCT Pub. No.: WO96/03108

PCT Pub. Date: Feb. 8, 1996

[30] Foreign Application Priority Data

Jul. 21, 1994 [GB] United Kingdom .................. 9414721

[51] Int. Cl.$^6$ ............................... A61K 7/16; A61K 7/18
[52] U.S. Cl. ............................................. 424/49; 414/52
[58] Field of Search ........................................ 424/49–58

[56] References Cited

U.S. PATENT DOCUMENTS

| | | |
|---|---|---|
| 3,939,261 | 2/1976 | Barth . |
| 3,954,962 | 5/1976 | Prussin . |
| 4,837,008 | 6/1989 | Rudy et al. . |
| 4,988,500 | 1/1991 | Hunter et al. . |
| 5,213,789 | 5/1993 | Degenhardt . |

FOREIGN PATENT DOCUMENTS

| | | |
|---|---|---|
| 8312717 | 9/1983 | Australia . |
| 333301 | 9/1989 | European Pat. Off. . |
| 420630 | 4/1991 | European Pat. Off. . |
| 2117240 | 10/1993 | United Kingdom . |

*Primary Examiner*—Shep K. Rose
*Attorney, Agent, or Firm*—Nora Stein-Fernandez; Janice E. Williams

[57] ABSTRACT

A non-aqueous dentifrice composition suitable as a vehicle for materials that are incompatible (i.e. have a limited solubility or react) with an aqueous enviroment. Accordingly, the present invention provides a non-aqueous dentifrice composition comprising a carboxyvinyl polymer, a humectant, a polyethylene glycol and a dentally acceptable abrasive.

8 Claims, No Drawings

DENTRIFICE COMPOSITION

This application is a 371 of PCT/EP95/02826 Jul. 18, 1995.

The present invention relates to a dentifrice composition, in particular to a non-aqueous (anhydrous) dentifrice composition. Such non-aqueous compositions may then suitably contain other materials which are unstable and incompatible with an aqueous environment.

There are many materials which have limited solubility in or even react with the aqueous systems of typical dentifrice formulations. One way of overcoming this problem during formulation is to encapsulate these water sensitive materials to prevent them from interacting with the aqueous component(s) present in the dentifrice formulation. Although encapsulation is a well known and used technique that can be usefully employed in the formulation of dentifrice compositions, it does not completely solve the problem as the encapsulated material frequently contacts water in the remainder of the product due to diffusion or 'capsule fracture'.

Other methods of improving the stability of these materials have been suggested and these include the use of anhydrous compositions.

U.S. Pat. No. 4,988,500 (Hunter et al) which has been assigned to The Procter & Gamble Company discloses and claims an anhydrous oral composition comprising a carboxyvinyl polymer, a neutralising agent, a peroxide or perborate compound and an anhydrous humectant. It is however necessary to neutralise the carboxyvinyl polymer in order to obtain dentifrice compositions that provide acceptable viscosity characteristics.

U.S. Pat. No. 4,647,451 (Piechota) which has been assigned to Colgate-Palmolive Company describes an anhydrous dentifrice containing a polysaccharide gum and a glycerine humectant. Polyethylene glycol is optionally added as a dispersion agent.

It has now been discovered that the problems associated with formulating and administering a dentifrice with ingredients that are incompatible with the aqueous phase may be solved by the use of an improved non-aqueous formulation that is as acceptable as conventional dentifrice formulations.

Accordingly, the present invention provides a non-aqueous dentifrice composition comprising a carboxyvinyl polymer, a humectant, a polyethylene glycol and a dentally acceptable abrasive.

The carboxyvinyl polymer is used in the acid form, and does not necessarily require any form of neutralising.

Carboxyvinyl polymers will thicken humectant materials and also provide the necessary rheology in order to suspend any required abrasive material.

The term 'rheology' as used herein is intended to reflect the flow characteristics of the formulation.

Suitable carboxyvinyl polymers for use in dentifrices of the invention are copolymers of acrylic acid cross-linked with polyallylsucrose, for example Carbopol 974 and 934 or cross-linked with divinyl glycol, for example Noveon AA-1. Carbopol polymers are manufactured by B.F. Goodrich Company. Carbopol 974 is preferred.

The carboxyvinyl polymer may be present in the range of from 0.1 to 7.5% w/w, preferably from 0.3 to 1.0%, more preferably about 0.35% by weight of the dentifrice.

Suitable humectants for use in the present invention include glycerine, sorbitol and propylene glycol or mixtures thereof. It is well known that commercially available glycerine may contain between 0.5–2.0% by weight of water which is in association with the glycerine. Typically this amount is between 0.5–1.0% by weight. This small amount of water if bound to the glycerine and is therefore not available to the other ingredients. The skilled person would still consider a composition containing glycerine as being non-aqueous. The humectants should in any case be as anhydrous as possible and preferably used in solid form.

Glycerine is the preferred humectant.

As the humectant is used to make the formulations up to 100%, the humectant may be present in the range of from 20 to 90% by weight of the dentifrice. Preferably the humectant is present from 35 to 75%, more preferably from 45 to 70% by weight of the dentifrice.

The polyethylene glycol is selected so that it will reduce any stickiness from the formulation and give a smooth textured product. Suitably, the polyethylene glycol will be selected from PEG 300 and PEG 400. PEG 400 is preferred.

Advantageously, the polyethylene glycol is present in the range of from 0.1 to 40%, preferably 15 to 20% by weight of the dentifrice.

It is perhaps more suitable to refer to the ratio of carboxyvinyl polymer to polyethylene glycol that is required in order to produce a product that is smooth and does not show any signs of stickiness.

Advantageously the ratio of carboxyvinyl polymer to polyethylene glycol is in the range of 1:15 to 1:20, preferably 1:17.5.

Suitable abrasives for use in the present invention include, for example, silica, zinc orthophosphate, sodium bicarbonate (baking soda), plastic particles, alumina, hydrated alumina, calcium carbonate and calcium pyrophosphate or mixtures thereof.

The silica abrasive may be a natural amorphous silica, for instance diatomaceous earth; or a synthetic amorphous silica such as a precipitated silica, for instance 'Tixosil 53B', manufactured by Rhone Poulenc, or a silica gel, such as a silica xerogel; or mixtures thereof.

Generally, an amount of abrasive suitable for use in the dentifrice composition of the present invention will be empirically determined to provide an acceptable level of cleaning and polishing, in accordance with the techniques well known in the art. Suitably, the abrasive will be present in from about 5 to about 60%, preferably from about 5 to about 30%, by weight of the dentifrice.

Advantageously a thickening agent is present in the formulation to give the product a rheology closer to that of a conventional dentifrice. Suitably the thickening agent is a thickening silica, for instance 'Sident 22S', which is manufactured by Degussa Ltd.

The thickening silica will be in the range of from 0.01 to 10%, preferably 5.0 to 7.0% by weight of the dentifrice.

Surfactant materials are usually added to dentifrice products to provide cleaning and/or foaming properties. Any conventional surfactant used in dentifrice formulations may be used in the present invention, provided that it can be added as a solid powder, that is not in an aqueous solution.

Suitable surfactants include anionic, cationic, nonionic and amphoteric surfactants.

Suitable nonionic surfactants include, for example polyethoxylated sorbitol esters, in particular polyethoxylated sorbitol monoesters, for instance, PEG(40) sorbitan diisostearate, and the products marketed under the trade name 'Tween' by ICI; polycondensates of ethylene oxide and propylene oxide (poloxamers), for instance the products marketed under the trade name 'Pluronic' by BASF-Wyandotte; condensates of propylene glycol; polyethoxylated hydrogenated castor oil, for instance, cremophors; and sorbitan fatty esters.

Suitable anionic surfactants include, for example sodium lauryl sulphate, marketed by Albright and Wilson and known as 'SLS'. This may be obtained and is used in a powder form in the present invention.

A particularly preferred anionic surfactant is sodium methyl cocyl taurate, marketed under the trade name 'Adinol CT 95' manufactured by Croda chemicals.

Advantageously, the surfactant is present in the range 0.005 to 20%, preferably 0.1 to 10%, more preferably 0.1 to 5% by weight of the dentifrice.

Advantageously a dentifrice according to the invention may further comprise an ionic fluorine-containing compound, which may include ionic fluorides, such as alkali metal fluorides, amine fluorides and ionic monofluorophosphates, such as alkali metal monofluorophosphates, and which may be incorporated into the formulation, to provide between 100 and 3000 ppm, preferably 500 to 2000 ppm of fluoride. Preferably the ionic fluoride or monofluorophosphate is an alkali metal fluoride or monofluorophosphate, for instance sodium fluoride or sodium monofluorophosphate, respectively. Stannous fluoride which is not used in conventional dentifrice formulations owing to its instability in an aqueous environment, may also be used at the above levels.

Calcium glycerophosphate which has been shown to enhance the activity of ionic monofluorophosphates, may be optionally added when the fluoride source is an ionic monofluorophosphate.

It will further be appreciated that if an ionic fluorine-containing compound is incorporated in a dentifrice of the invention, the abrasive should be chosen so that it is compatible with the ionic fluorine-containing compound. Thus, for instance, sodium fluoride is well known in the art to be incompatible with abrasives with comprise excess calcium ions as these cause loss of fluoride as insoluble calcium fluoride. Accordingly an abrasive which is insoluble, for instance, a silica, alumina, zinc orthophosphate or plastic particles, is preferred. Alternatively, a calcium abrasive, for instance calcium carbonate, may be used with an alkali metal monofluorophosphate, sodium monofluorophosphate.

Dentifrices according to the invention may also contain other agents conventionally used in dentifrice formulations, for example colouring agents, whitening agents, for example titanium dioxide; preservatives and sweetening agents. Anti-plaque agents, for example triclosan, chlorhexidine, cetyl pyridinium chloride and nicin (preferably in a purified form, and available as Ambicin N), anti-calculus agents, for example pyrophosphate salts, anti-sensitivity agents, for example strontium or potassium salts, polymer enhancing agents, for example Gantrez may also be present if required. Breath freshening agents, for example, sodium bicarbonate and tooth whitening agents, for example hydrogen peroxide and sodium tripolyphosphate may also be included at appropriate levels.

In general, such agents will be in a minor amount or proportion of the formulation, usually present in from 0.001 to 5% by weight of the composition. Any active ingredient or combination of actives that are unstable or incompatible in any way with aqueous environments may also be added to the formulation of the present invention. Flavouring agents may also be added to the formulations, usually at a typical level of 1.0% by weight of the composition.

Suitable sweetening agents include saccharin, cyclamate and acesulfame K, and may be present in from 0.01 to 0.5%, preferably 0.05 to 0.5% by weight of the dentifrice. An auxiliary sweetener such as a thaumatin may also be included, at a level of from 0.001 to 0.1, preferably 0.005 to 0.05% by weight of the dentifrice. A suitable blend of thaumatins is marketed under the trade name 'TALIN' by Tate and Lyle plc.

Dentifrices according to the invention may also contain an antistain agent. Suitable antistain agents include, for example, carboxylic acids such as those disclosed in U.S. Pat. No. 4,256,731, amino carboxylate compounds such as those disclosed in U.S. Pat. No. 4,080,441 and phosphonoacetic acid, as disclosed in U.S. Pat. No. 4,118,474. The antistain agent may be incorporated into the dentifrice formulation or may be provided as a separate composition, for use after the dentifrice.

The dentifrices according to the invention may have an initial viscosity of 25,000 to 100,000 centipoise which is essential for producing a product that is comparable to conventionl dentifrices that have consumer acceptability. The pH of the formulation when diluted in the ratio of 3:1 with water should be less than 8.0.

The viscosity of the dentifrice is measured using a TF 20 spindle Brookfield Viscometer.

The dentifrices according to the invention may be prepared in a conventional manner by mixing the ingredients thereof in the required proportions and in any order which is convenient and, thereafter and if necessary, adjusting the pH. In a particularly preferred process the polyvinyl polymer and the humectant are vigourously agitated together, with heat, for example to a temperature of for example 50°–70° C., if neccessary, in order to give a satisfactory viscosity. Polyethylene glycol and a thickening silica are then added to the mixture and abrasive is then dispersed in it, using a heavy-duty mixing machine. Active agents, such as a fluoride salt (if present) are then added, followed by surfactant and flavouring agents in the final stage; with final mixing carried out under vacuum.

The following examples illustrate the invention.

EXAMPLE 1

| INGREDIENT | % w/w |
|---|---|
| CARBOPOL 974P | 1.00 |
| THICKENING SILICA | 4.00 |
| ABRASIVE SILICA | 14.00 |
| SODIUM FLUORIDE | 0.23 |
| TITANIUM DIOXIDE | 1.00 |
| ADINOL CT 95 | 2.00 |
| SACCHARIN | 0.33 |
| POLYETHYLENE GLYCOL(400) | 17.50 |
| FLAVOUR | 1.00 |
| GLYCERIN | qs |

EXAMPLE 2

| INGREDIENT | % w/w |
|---|---|
| CARBOPOL 974P | 1.00 |
| THICKENING SILICA | 6.50 |
| ABRASIVE SILICA | 14.00 |
| SODIUM FLUORIDE | 0.23 |
| TITANIUM DIOXIDE | 1.00 |
| ADINOL CT 95 | 2.00 |
| SACCHARIN | 0.33 |
| POLYETHYLENE GLYCOL(400) | 17.50 |
| GLYCERIN | qs |

EXAMPLE 3

| INGREDIENT | % w/w |
|---|---|
| CARBOPOL 974P | 0.50 |
| THICKENING SILICA | 6.50 |
| ABRASIVE SILICA | 14.00 |
| SODIUM FLUORIDE | 0.23 |
| TITANIUM DIOXIDE | 1.00 |
| ADINOL CT 95 | 2.00 |
| SACCHARIN | 0.33 |
| POLYETHYLENE GLYCOL(400) | 17.50 |
| GLYCERIN | qs |

EXAMPLE 4

| INGREDIENT | % w/w |
|---|---|
| CARBOPOL 974P | 0.35 |
| THICKENING SILICA | 6.50 |
| ABRASIVE SILICA | 14.00 |
| SODIUM FLUORIDE | 0.23 |
| TITANIUM DIOXIDE | 1.00 |
| ADINOL CT 95 | 2.00 |
| SACCHARIN | 0.33 |
| POLYETHYLENE GLYCOL(400) | 17.50 |
| GLYCERIN | qs |

EXAMPLE 5

| INGREDIENT | % w/w |
|---|---|
| CARBOPOL 974P | 0.35 |
| THICKENING SILICA | 6.50 |
| ABRASIVE SILICA | 14.00 |
| SODIUM FLUORIDE | 0.23 |
| TITANIUM DIOXIDE | 1.00 |
| ADINOL CT 95 | 2.00 |
| SACCHARIN | 0.33 |
| POLYETHYLENE GLYCOL(400) | 6.20 |
| GLYCERIN | qs |

Carbopol 974 P is a Tradename of Goodrich plc.
Adinol CT 95 is a Tradename of Croda Chemicals.

We claim:

1. A non-aqueous, non-stringy, smooth textured, non-sticky paste dentifrice composition comprising 0.1% to 7.5% by weight of an unneutralized carboxyvinyl polymer in the acid form, an anhydrous humectant, 0.1 to 40% by weight of a polyethylene glycol solvent for said unneutralized carboxyvinyl polymer imparting smooth texture and reduced stickiness and a dentally acceptable abrasive and thickening silica wherein the ratio of carboxyvinyl polymer to polyethylene glycol is 1:15 to 1:2, and wherein the initial viscosity of the dentifrice ranges between 25,000 and 100,000 centipoise.

2. A composition according to claim 1, wherein the carboxyvinyl polymer is a copolymer of an acrylic acid crosslinked with polyallylsucrose or divinylglycol.

3. A composition according to claim 1, wherein the carboxyvinyl polymer is present in an amount of from 0.1 to 7.5% by weight of the dentifrice.

4. A composition according to claim 1, wherein the anhydrous humectant is glycerine, sorbitol or propylene glycol or mixture-thereof.

5. A composition according to claim 4, wherein the anhydrous humectant is present in a range of from 20 to 90% by weight of the dentifrice.

6. A composition according to claim 1 wherein the abrasive is selected from silica, zinc orthophosphate, sodium bicarbonate, plastic particles, alumina, hydrated alumina, calcium carbonate or calcium pyrophosphate or mixtures thereof.

7. A composition according to claim 1 additionally comprising from 0.01–10% by weight of a thickening silica.

8. A process for the preparation of a composition according to claim 1 wherein the carboxyvinyl polymer and the anhydrous humectant are vigorously agitated together, with heat to give a satisfactory viscosity, after which the remaining ingredients are mixed in the required proportions.

* * * * *